(12) United States Patent
Dolan et al.

(10) Patent No.: US 12,059,162 B2
(45) Date of Patent: Aug. 13, 2024

(54) WIRE FOR AN ENDOVASCULAR APPARATUS

(71) Applicant: Versono Medical Limited, Galway (IE)

(72) Inventors: Finbar Dolan, Galway (IE); Hugh O'Donoghue, Galway (IE); Ivan Mooney, Galway (IE); Pat Connolly, Galway (IE); Jim Smedley, Galway (IE); Brian Tarpey, Galway (IE)

(73) Assignee: Versono Medical Limited, Galway (IE)

( * ) Notice: Subject to any disclaimer, the term of this patent is extended or adjusted under 35 U.S.C. 154(b) by 0 days.

(21) Appl. No.: 17/662,304

(22) Filed: May 6, 2022

(65) Prior Publication Data

US 2022/0257270 A1 Aug. 18, 2022

Related U.S. Application Data

(63) Continuation of application No. PCT/EP2020/081399, filed on Nov. 6, 2020.

(30) Foreign Application Priority Data

Nov. 6, 2019 (WO) ................. PCT/EP2019/080449
May 5, 2020 (GB) ..................................... 2006665

(51) Int. Cl.
*A61B 17/22* (2006.01)
*A61B 17/00* (2006.01)
*A61B 90/00* (2016.01)

(52) U.S. Cl.
CPC .... *A61B 17/22012* (2013.01); *A61B 17/2202* (2013.01); *A61B 90/39* (2016.02);
(Continued)

(58) Field of Classification Search
CPC .... A61B 17/22012; A61B 2017/22015; A61B 2017/320098; A61B 17/3211;
(Continued)

(56) References Cited

U.S. PATENT DOCUMENTS 3,433,226 A 3/1969 Boyd
4,979,939 A 12/1990 Shiber
(Continued)

FOREIGN PATENT DOCUMENTS

JP H06-105914 A 4/1994
JP 2002-85420 A 3/2002
(Continued)

OTHER PUBLICATIONS

International Search Report and Written Opinion in International Application No. PCT/EP2020/081399, mailed Mar. 2, 2021 (14 pages).

*Primary Examiner* — Katherine H Schwiker
*Assistant Examiner* — Lauren Dubose
(74) *Attorney, Agent, or Firm* — Bookoff McAndrews, PLLC

(57) ABSTRACT

An elongate endovascular element for crossing through an obstruction in a blood vessel comprises: a proximal section; a distal tip section of smaller diameter than the proximal section; and a distally-tapering intermediate section extending between the proximal and distal tip sections; wherein the tapered intermediate section has a length that is substantially $\lambda/2$ or a multiple of $\lambda/2$, where $\lambda$ is a wavelength of a driving frequency that will produce longitudinal resonance in the element.

18 Claims, 14 Drawing Sheets

(52) U.S. Cl.
CPC .............. *A61B 2017/00477* (2013.01); *A61B 2017/22014* (2013.01); *A61B 2017/22015* (2013.01); *A61B 2017/22017* (2013.01); *A61B 2017/22027* (2013.01); *A61B 2017/22041* (2013.01); *A61B 2017/22044* (2013.01); *A61B 2017/22049* (2013.01); *A61B 2017/22094* (2013.01); *A61B 2090/0808* (2016.02); *A61B 2090/3966* (2016.02); *A61B 2217/007* (2013.01)

(58) Field of Classification Search
CPC ............ A61B 17/320068; A61B 18/04; A61B 2017/320078; A61B 2017/00106; A61B 2017/22094; A61B 2017/320088; A61B 17/2202; A61B 2017/00477; A61B 2017/22039; A61B 2017/22049; A61B 17/320708; A61B 2017/00469; A61B 2017/22014; A61B 2017/22038; A61B 2017/22044; A61B 90/39; A61B 2090/0808; A61B 2090/3966; A61B 2090/0807; A61B 2017/22017; A61B 2017/22027; A61B 2017/320069; A61B 2017/320072; A61B 2017/320073; A61B 17/22004; A61B 2018/00607; A61N 7/00; A61N 2007/0073

See application file for complete search history.

(56) References Cited

U.S. PATENT DOCUMENTS

| | | | |
|---|---|---|---|
| 5,161,534 A | 11/1992 | Berthiaume | |
| 5,243,997 A | 9/1993 | Uflacker et al. | |
| 5,248,296 A | 9/1993 | Alliger et al. | |
| 5,284,148 A | 2/1994 | Dias et al. | |
| 5,382,228 A | 1/1995 | Nita et al. | |
| 5,427,118 A | 6/1995 | Nita et al. | |
| 5,524,635 A | 6/1996 | Uflacker et al. | |
| 5,542,917 A | 8/1996 | Nita et al. | |
| 5,549,582 A * | 8/1996 | Larsson | A61M 39/223 604/533 |
| 5,846,218 A | 12/1998 | Brisken et al. | |
| 5,908,395 A | 6/1999 | Stalker et al. | |
| 5,971,949 A * | 10/1999 | Levin | A61B 17/320068 606/169 |
| 6,007,514 A | 12/1999 | Nita | |
| 6,010,449 A | 1/2000 | Selmon et al. | |
| 6,241,703 B1 | 6/2001 | Levin et al. | |
| 6,251,110 B1 * | 6/2001 | Wampler | A61B 18/1402 606/49 |
| 6,450,975 B1 | 9/2002 | Brennan et al. | |
| 6,577,042 B2 | 6/2003 | Lee et al. | |
| 6,695,782 B2 | 2/2004 | Ranucci et al. | |
| 6,855,123 B2 | 2/2005 | Nita | |
| 9,282,984 B2 | 3/2016 | Nita | |
| 9,629,643 B2 | 4/2017 | Nita | |
| 2004/0024402 A1 | 2/2004 | Nita | |
| 2004/0127791 A1 | 7/2004 | Mast et al. | |
| 2004/0260180 A1 | 12/2004 | Kanai et al. | |
| 2005/0119679 A1 * | 6/2005 | Rabiner | A61B 17/22012 606/159 |
| 2007/0066978 A1 | 3/2007 | Schafer et al. | |
| 2007/0185501 A1 | 8/2007 | Martin et al. | |
| 2008/0228111 A1 | 9/2008 | Nita | |
| 2009/0292296 A1 | 11/2009 | Pansky et al. | |
| 2011/0040213 A1 * | 2/2011 | Dietz | B06B 3/00 601/2 |
| 2011/0196384 A1 | 8/2011 | Pansky | |
| 2014/0128863 A1 | 5/2014 | Song | |
| 2014/0270430 A1 | 9/2014 | Nair | |
| 2017/0215837 A1 | 8/2017 | Ramakrishna | |
| 2019/0125302 A1 | 5/2019 | Clark | |
| 2019/0262016 A1 | 8/2019 | Zheng et al. | |
| 2022/0313293 A1 * | 10/2022 | Singh | A61B 17/320068 |

FOREIGN PATENT DOCUMENTS

| | | |
|---|---|---|
| JP | 2005-507735 A | 12/2005 |
| JP | 2009-586 A | 1/2009 |
| JP | 2015-524315 A | 8/2015 |
| WO | 9509572 A1 | 4/1995 |
| WO | 2006059966 A1 | 6/2006 |
| WO | 2006120674 A1 | 11/2006 |
| WO | 2009141810 A2 | 11/2009 |
| WO | 2014022716 A2 | 2/2014 |
| WO | 2016081025 A1 | 5/2016 |
| WO | 2016081026 A1 | 5/2016 |
| WO | 2019094028 A1 | 5/2019 |
| WO | 2019152898 A1 | 8/2019 |
| WO | 2020094747 A2 | 5/2020 |
| WO | 2021089847 A1 | 5/2021 |
| WO | 2021089859 A2 | 5/2021 |
| WO | 2022129623 A1 | 6/2022 |

* cited by examiner

WIRE FOR AN ENDOVASCULAR APPARATUS

CROSS-REFERENCE TO RELATED APPLICATIONS

This application is a continuation of International Application No. PCT/EP2020/081399, filed on Nov. 6, 2020, which claims the benefit of priority to International Application No. PCT/EP2019/080449, filed on Nov. 6, 2019, and GB Application No. 2006665.0, filed on May 5, 2020. The contents of each of these are incorporated herein by reference.

TECHNICAL FIELD

The present invention relates to treatment of ischaemia by using an ultrasonically activated wire or other elongate element to cross through a blockage in a blood vessel and to facilitate the introduction of follow-on therapeutic devices.

PRIOR PATENT APPLICATIONS

The invention develops concepts expressed in our International Patent Application published as WO 2020/094747, and the yet unpublished GB patent application no. 2006665.0 whose contents are incorporated herein by reference.

BACKGROUND

In endovascular procedures, an artery is selected and recruited for use in obtaining access to the vasculature. The selection is based on the artery's ability to accommodate the passage of the intended diagnostic or therapeutic device to the target site and the extent to which it may minimise tissue and patient trauma.

In revascularising procedures, for example in peripheral arteries or veins, access is often made by surgical cutdown and puncture to the femoral, popliteal, tibial and/or pedal arteries, commonly known in medical terms as the Seldinger technique. Once the access is made, an introducer wire and an introducer sheath are inserted into the vessel and secured at the site. This sheath acts as a port for the introduction, withdrawal and exchange of devices and serves to minimise abrasion of the arterial tissue. Then guide catheters and guidewires are introduced into the artery, to provide further protection and to assist device navigation and provision of therapy to the target site.

Guidewires are pushed along the lumen of the vessel, carefully to avoid causing any trauma to the vessel wall, and are navigated to the site of the obstruction. In successful procedures, the guidewires are then pushed across, or through, the obstruction and are kept in situ to act as a guide over which the diagnostic or therapeutic devices, such as balloon catheters and stents, are tracked to the site of the occlusion. Guidewires are used in other minimally-invasive procedures to introduce other devices and instruments into vessels or other cavities of the body to enable inspection, diagnosis and different types of treatment.

Guidewires are, for example, used for balloon angioplasty, gastrointestinal, urological, and gynaecological procedures. All such procedures require a passageway to be formed through a blockage to facilitate the passage of larger and often more cumbersome devices to the site of lesions or other tissues targeted distal to the lesions in the body.

Guidewires are key to therapeutic intervention and are manufactured from different materials, most typically stainless steels and various alloys, including NiTi (nitinol), cobalt-chrome (CoCr) etc., with many different designs. Their manufacture often involves the modification of the chemical composition and microstructural morphology of the material, for example by cold working the material while forming it into a wire and then machining the wire to different dimensional designs and applying different thermal treatments to effect a desirable performance. As an example, specific tapers may be machined over the length of a wire to produce differential degrees of flexibility along the length of the wire. So, at its distal end, the wire will have sufficient flexibility to conform to the shape of the vessel, and strength to transmit force to the tip ('tip stiffness') or force to cross through the lesion.

In conventional guidewires, the tapered segments are encased in coils or jacketing materials that allow for flexibility through the tapers while enabling transmission of force to the distal tip of the wire through the coils. As will be explained, in wires of the invention, such coils or jacketing materials are not essential as force is transmitted by ultrasonic energy to excavate a lumen even if the wire is uncoated or unjacketed.

The length of wires used in endovascular procedures varies depending on the distance over which they are considered likely to operate. As an example, wires typically of 750 mm up to 900 mm in length are used in many peripheral applications where they may be introduced in femoral or popliteal anatomies, or need to track to and through blockages in ipsilateral iliac femoral popliteal and infra popliteal arteries. Wires that are used in ipsilateral and coronary applications tend to be of the order of 1200 mm, 1500 mm or 1700 mm in length. Indeed, wires that may be tracked contra laterally may be longer, perhaps of the order of 2000 mm to 2250 mm or 2500 mm or 3000 mm in length. The most common wire lengths on the market are 1750 mm, 1950 mm and 3000 mm.

In many instances extension wires may be used to facilitate the deployment of certain therapeutic devices, referred to as over the wire (OTW) devices. In this instance the proximal end of the wire may require certain features.

Many conventional endovascular wires are passive mechanical devices with no active components. Passive wires do not transmit any energy other than that applied by the clinician. They are operated by their proximal end being pushed, pulled, and torqued to navigate to the blockage site and are then pushed through or around the blockage. They are of varied constructions and designs to facilitate access and crossing of lesions in different anatomies and for different devices. However, in very many instances the occlusions are too challenging for conventional wires to cross through. These passive wires then do not work as guidewires are intended to, or they are limited when trying to cross nearly- or totally-occluded blockages that may also be significantly calcified. In situations where they are tracked around occlusions, e.g. in a sub-intimal situation, such wires are often unsuccessful at re-entering the true lumen.

The present invention relates to the use of ultrasonic vibrations transmitted along wires to cross blockages. Transmission of ultrasonic vibrations along small-diameter catheters and assemblies is disclosed in U.S. Pat. No. 3,433,226. U.S. Pat. No. 5,971,949 describes the transmission of ultrasonic energy via waveguides of different configurations and tip geometries. U.S. Pat. No. 5,427,118 describes an ultrasonic guidewire system but does not discuss in detail proximal geometries of the wire or how it facilitates follow-on devices via over-the-wire methods.

Many current single-transducer systems are not ultrasonically activated guidewires but are instead, ultrasonically activated catheters that contain wire members to agitate and ablate material. U.S. Pat. Nos. 6,855,123 and 4,979,939 describe such systems. These catheters themselves require a separate passive guidewire to help them navigate and, as such, are tools to facilitate a separate guidewire crossing a blockage. U.S. Pat. No. 9,629,643 shows a system with a range of distal tip configurations but all requiring a separate guidewire for access.

These devices are directed towards delivering an alternative method of revascularisation and are often described as atherectomy devices, crossing devices or vessel preparation devices. With limited exceptions, they do not identify with crossing through lesions with the purpose of acting as a device delivery system. In the art, these ultrasonic devices and recanalisation wire devices enhance revascularisation and provide for, or effect, an atherectomy by de-bulking the lesion by removing the plaque that forms the lesion.

In the early, later and current designs, ultrasonic generator systems are large because of the acoustics used and they have become large units, scaled to generate multiple frequencies and to control the pulsed wave. Also, practical utility considerations mean that known systems commonly comprise separate elements. For example, many systems are designed with the signal generator housed in a separate unit from a transducer, some being mounted on large trolley units, consoles or stands that take up significant space in the clinical environment. U.S. Pat. No. 6,450,975, US 2008/0228111 and U.S. Pat. No. 9,282,984 all describe such systems.

Ultrasonically-activated catheter and wire systems have been considered in the past as a method of crossing or atherectomy and to prepare vessels for angioplasty treatment. Some products have been made available commercially in the past, some remain available on the market and some new systems have come to market recently. Such catheter and wire systems often include an ultrasonic generator and an ultrasonic transducer. The ultrasonic generator converts mains electricity into an ultrasonic waveform, defined by its voltage amplitude, current and frequency. The ultrasonic transducer, and often an amplifying horn, convert the electrical energy into high-frequency mechanical vibrations, defined by frequency and amplitude of vibration.

A small-diameter wire waveguide is coupled at its proximal end directly to the transducer, or via any horn, and transmits the mechanical vibrations to the distal tip of the wire. This results in the distal tip of the wire waveguide vibrating at a desired amplitude and frequency with the goal of excavating material and ultimately facilitating the revascularisation or recanalisation of vessels and anatomical structures throughout the body. Tissue and material in the vicinity of the distal tip are affected by a combination of the ultrasonic movement of the tip and its direct mechanical abrasion, ablation and cavitation from the pressure wave components and acoustic streaming that removes ablated material from the zone around the tip.

In known ultrasonically activated endovascular wire systems, the proximal end of the guide wire is connected to the transducer. In our patent application published as WO 2020/094747, the wire runs through the transducer and not only extends distally therefrom, but also proximally. This allows the user to couple the transducer to the wire at any desired position and to adjust the total length of the distal portion of the wire, without having to cut it. The ability of the wire to travel or extend through the transducer and to be coupled to the transducer at a plurality of locations has very useful practical benefits arising from the ability to adjust the total length of the distal portion of the wire, for example to adapt to the expected length of the trajectory the wire tip needs to travel within the patient's body. Also, control of the wire is enhanced in keeping its placement in situ in the vascular lumen whilst adjusting or reconnecting activation source. Additionally, an adjustable-length distal portion of the wire helps for achieving and optimising resonance at the distal tip at any desired frequency.

In developing the concepts disclosed in WO 2020/094747, the inventors have recognised a need for pre-existing endovascular wires to be improved in various respects, whether for use with the concepts of WO 2020/094747 or otherwise. There is a need for endovascular wires that can be manufactured more easily, that can be navigated more easily to the site of a lesion, that can be activated and controlled more simply and effectively, and that can cross through the lesion more efficiently while forming a larger lumen that is better able to facilitate flow along a vessel and to accommodate follow-on therapies.

It is an aim of the present invention to address one or more disadvantages associated with the prior art.

SUMMARY OF THE INVENTION

According to an aspect of the invention there is provided an elongate endovascular element for crossing through an obstruction in a blood vessel. The element comprises:
- a proximal section;
- a distal tip section of smaller diameter than the proximal section; and
- a distally-tapering intermediate section extending between the proximal and distal tip sections;
- wherein the tapered intermediate section has a length that is substantially $\lambda/2$ or a multiple or an even-denominator fraction of $\lambda/2$ in the sequence $\lambda/4, \lambda/8 \ldots$, where $\lambda$ is a wavelength of a driving frequency that will produce longitudinal resonance in the element.

The invention also resides in an endovascular apparatus for crossing through an obstruction in a blood vessel, the apparatus comprising an elongate endovascular element of the invention and an ultrasonic transducer, mechanically coupled to that element, for ultrasonically exciting the distal tip section thereof to facilitate crossing through the obstruction.

The invention also provides a method of ultrasonically exciting a distal tip section of an elongate waveguide element, the method comprising: inputting ultrasonic energy into a proximal section of the element at a driving frequency that excites longitudinal resonance in the element; and generating lateral sub-harmonic vibrations in the distal tip section in addition to longitudinal vibrations.

The ultrasonic excavating guidewire of the invention differs from other ultrasonic wires and conventional guidewires in various important aspects.

The invention assists with navigating the wire through the anatomy, crossing through a lesion and opening out a lumen whose diameter is greater than the diameter of the wire or a bulb or any other enlarged feature at a distal end of the wire. For this purpose, the distal end portion, which may be tapered or of narrower diameter than a proximal portion of the wire, is left bare to facilitate lateral excavation in the distal region. In conventional wires and in competing ultrasonic guidewires, the distal end of the wire is tapered down to a narrow diameter to help the wire to navigate through tortuous anatomies. However, these portions of the wires are sleeved-over with spring-like coils and or with polymer jackets to enable such flexible elements to be pushed through the anatomy.

The coil or jacket of prior art wires allows for the transmission of longitudinal load and may have a secondary function of maintaining a constant diameter over the length of the wire so that follow-on therapeutic devices that are introduced into the vasculature over the guide wire can do so over a maximum working length. However, in the ultrasonic wire of the invention, energy in the form of an ultrasonic displacement waveform transmitted through the wire provides a means to enable the wire to pass through obstructions and therefore coils or jackets in the distal end portion of the wire are not essential.

To provide for lateral excavation of occluding materials, the absence of distal coils or jackets and the optimisation of the tapered and distal land length and diameter in the invention provide for dual excavation by longitudinal and lateral displacement of the wire effecting cavitation, abrasion and ablation. The invention allows preferential selection of subharmonics in the lateral or radial direction in addition to longitudinal direction.

To select subharmonic frequencies at the distal end that will excavate in the lateral mode, the distal end portion of the wire is machined in form in accordance with the invention to suit preferential selected dominant subharmonic resonant frequencies. This maximises lateral displacement of the distal end portion through the design of the shaped profile of the wire with respect to its taper and the length of its distal land length and diameter.

For a given material selected for its resilience, toughness and mechanical properties with a characteristic acoustic performance at 37 C, the optimal characteristic of the wire in respect to gross length is to be an odd multiple (n=1, 3, 5, . . . n) of $\lambda/4$, where $\lambda$ is the wavelength in the material for a given input frequency and specific material properties.

The transition of a taper provides a step gain or amplification in the ultrasonic energy transmitted distally in the wire. However, the inventors have noted that the natural selection of a dominant sub-harmonic can be effected by making the taper length $\lambda/2$. It has also been found that optimal lateral transmission of the wire is obtained through a distal land length of $\lambda$.

An important aspect that determines usability is that wires of the invention have tip flexibility allowing them to conform to the shape of the arteries or other vessels that they navigate and to be flexible so that the lateral mode of oscillation effects a significant force displacement. Thus, wires with a distal land diameter of 0.005" to 0.008" are preferred, with 0.007" providing optimal performance in Type 1 Nitinol wire with a particular $A_f$, e.g. between 5° C. and 18° C.

It is necessary to utilise the excitation-established modes of displacement in the longitudinal and lateral directions without exposing the wire to elevated levels of stress or strain that could cause the wire to fracture catastrophically. Thus, the wire is mechanically coupled to the ultrasonic transducer and is predominantly excited in the longitudinal direction at a prescribed frequency and amplitude of displacement. The wire geometry is selected to resonate mainly in the longitudinal mode at or near this input driving frequency, which sets up a standing wave in the wire along its length while in resonance. This results in a significant longitudinal component of vibration in the vicinity of the distal tip.

Another challenge is that whilst the lateral mode of displacement can occur anywhere along the length of the wire, it is desirable to convey and to focus energy toward the distal end. In particular, in addition to the longitudinal mode at or near to the driving frequency of the system, there will be various additional longitudinal sub-harmonics at which a wire of a length suitable for anatomical entry will be excited. Further, the wire has lateral or transverse modes of vibration near the longitudinal primary frequency and its sub-harmonic frequencies. Any offset or imbalance introduced in the wire's anisotropy or conformation or geometry will promote these lateral modes of vibration, especially if these lateral modes are at or near the longitudinal modes. However, it is desirable to encourage lateral excitation to occur preferentially in the distal region of the wire.

Lateral displacements occur at frequencies lower than the drive or input frequency and their attenuation and amplification of the movement in the wire is dominated by the driving frequency and the geometry and materials used in the wire. Such lateral modes are superimposed on the longitudinal motion of the distal region and in accordance with the invention may be selected preferentially by incorporating particular design features into the wire. Whilst in principle these lateral displacements may be present in the wire, the selection of specific frequencies and modes of vibration can be achieved by tailoring the geometry of the wire, including the position and length of tapers, and the magnitude of the movement can be determined by the diameter and material properties of the distal portions of the wire.

There is a need to optimise the wire to get the wire to displace with an optimal level of force and displacement to excavate a blockage. Thus, in optimised wires of the invention, the construction of the different tapers and different lands along the length of the wire can effect different lateral and longitudinal responses in the distal end region of the wire. These responses can then be optimised for the different use cases envisioned in different anatomies and with different types of lesions.

There is also a need for guidewires that can quickly navigate to and through chronic total occlusions that are composed of hard calcific lesions and to so provide a lumen large enough to allow the passage of follow-on therapeutic devices over the wire. Thus, an objective of the invention is selectively to excavate occluding materials within a blood vessel and to open an aperture or lumen substantially greater than the cross-sectional area of the wire to facilitate the delivery of a follow-on therapy. To this end, the mechanisms of excavation in the distal tip region of the wire comprise direct longitudinal vibration coupled to lateral motion that act in unison to ablate and open a lumen in the lesion. This ablation or other excavation mechanisms may occur not only where the distal tip of the wire contacts the lesion but also where the distal region of the wire contacts the lesion after first penetrating the lesion.

Various inter-relating variables can be modified in accordance with the invention to optimise excavation of a lesion. Specifically, the wire directs ultrasonic energy from where the wire is coupled to the transducer to the distal end of the wire. Excavation at this distal tip region of the wire is determined by the mode (i.e. lateral and longitudinal movement) and amplitude in which the energy is presented in the wire and so by: the driving frequency and amplitude driving the ultrasonic signal/displacement in the wire through its length; the characteristic of acoustic transmission in the wire; and the diameters of the different sections of the wire, namely in a proximal land section, in an intermediate tapered section and in a distal land section, affecting amplification and the amplitude of wire displacement in the different regions along the length of the wire as it responds to excitation.

Thus, the dimensions and uniformity of the wire influence its response, in terms of: the internal composition of the wire and the nature of its material; the external shape of the wire and any discontinuity or shaped feature or formation in the wire; the uniformity of the wire in terms of its shape and dimensions, such as tolerances over length; the taper dimensions, transition sections and their relevance to the applied ultrasonic energy; changes in the diameter of the wire from its proximal diameter at the transducer to the diameter of its distal excavating land; the amplification associated with this reduction in diameter over the length of the wire; and the location and length of the tapered section and how it corresponds to wavelength.

Selecting the mechanical properties and design of the wire to optimise its performance recognises that these attributes are relevant to the physical manifestation of transverse or lateral motion.

All of these objectives of the invention have to be achieved with a wire that is also flexible enough to confirm to the shape of the anatomy through which it passes in use. In particular, the flexibility and elasticity or resilience of the wire determines whether the wire can fit within the lumen of an artery or other vessel. The diameter and mechanical strength of the wire also determines whether the wire can track through, or navigate through, tortuous anatomy and so follow the shape of the vessel and not jam, stall or, worse, penetrate the wall of the vessel, due to being unable to deflect and to adopt the shape of the anatomy. In this respect, in the case of femoral arteries the vessels are large and so the ability of the wire to conform to their shape is less challenging than, for example, in the pedal arteries, whose tortuosity is similar to that of coronary arteries and some of the larger neurovascular anatomies.

Collectively, wire design parameters can be selected to control how much energy is coupled into the longitudinal modes and lateral modes. In preferred embodiments, the ratio of the diameter of the proximal segment defining the working length of the wire to the diameter of the distal segment defining the excavating section of the wire is between 2:1 and 3:1, which offers an optimal gain or amplification.

The optimal length of the tapered section to select the a dominant secondary frequency is $\lambda/2$, i.e. the ratio of the length of the tapered section to the length of the distal land length is $\lambda/2:\lambda$ with the effective length of the wire from the coupling to the distal tip being an odd multiple of $\lambda/4$ (($2n+1$) $\lambda/4$).

A wire is an example of an elongate endovascular element of the invention that may be used as a waveguide or wave delivery system. For example, the element could be a hybrid of a wire and a catheter. In particular, a proximal portion of the element, for example about the first metre of the element from the proximal end, could have a wire encapsulated in a manner akin to a catheter whereas a distal portion of the element extending to the distal end could be an unencapsulated wire. A wire or other element of the invention could be the inner component of an overall wave delivery system.

The design of the transmission member or waveguide wire is optimised to control the transmission of the wave pattern through different anatomies to the distal tip and through different materials. The morphology of the materials used is critical and whilst they can, at a 'macroscopic' level, present as an isotropic material morphology that is highly resilient, they can have anisotropic micromorphological features that can either delay the onset of a starter crack or inhibit the progression of a crack.

The materials used in the embodiments are extensively cold-worked stainless steels, nickel titanium alloys and/or cobalt/chromium alloys, e.g. linear elastic nitinol. Specifically, in the case of the NiTi only alloys, tight control is exercised over the inclusion size and population in order to limit the likelihood of fracture. In other alloys, control is exercised over other morphological features that may act to promote premature failure of the wire.

The invention allows for the introduction of specific features that are machined into the wire at the proximal and the distal end and over its length to enhance its ability to cross through the lesion, to strengthen the wire, to enable greater control over the wire, to enable coupling of the wire and efficient transmission through the wire. The composition of the designs varies with materials used and the intended use.

The geometry of the wire as well as the materials used are optimised for different application use cases. The wires are machined to minimize defects and to optimise the transmission through tightly controlled tapers and keying splines over the length and through sections of the length of the material.

BRIEF DESCRIPTION OF THE DRAWINGS

Embodiments of the invention will now be described by way of example with reference to the accompanying drawings, in which.

DETAILED DESCRIPTION

Figure 1:
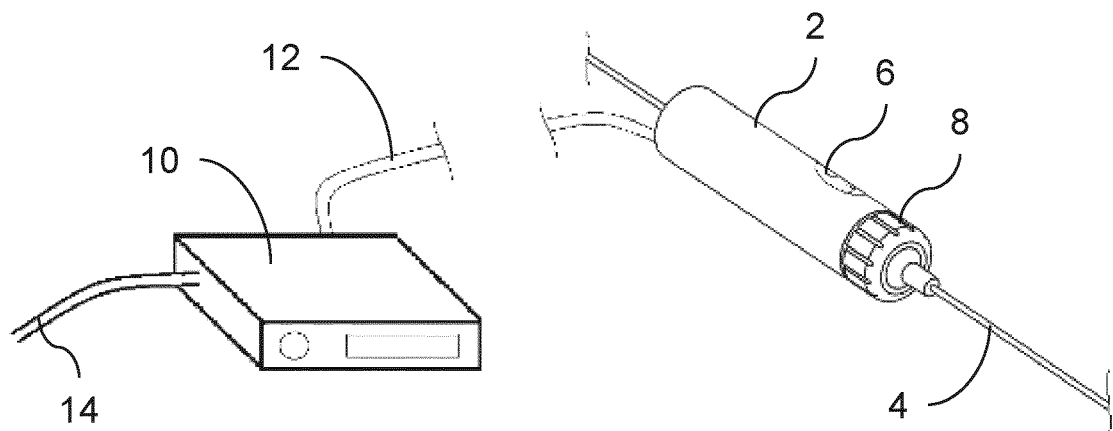
FIG. 1 is a schematic perspective view of an ultrasonic wire system according to the invention.

FIG. 1 of the drawings shows the overall configuration of a system according to the invention and illustrates some major components of such a system. This example features a handheld ultrasonic activation unit 2 through which a flexible transmission member in the form of an endovascular wire 4 extends, in central alignment.

The wire 4 can be inserted into a patient's vasculature and traversed to bring its distal end to the location of a lesion. Once a complex lesion is encountered that resists the wire 4 crossing it, the activation unit 2 can be coupled to the wire 4 at a suitable longitudinal location. When activated, the activation unit 2 transmits ultrasonic vibrations to and along the wire 4, enhancing the ability of the wire 4 to cross the lesion through ablation and other mechanisms. The wire 4 thereby serves as a crossing wire for crossing through an occlusion in a blood vessel and can then remain in situ to serve as a guide wire for delivering subsequent therapeutic devices to treat the lesion.

Typically, the wire 4 may, for example, be more than 2 m and up to 3 m in length. For example, access to a lesion in or through the foot may involve the wire travelling a distance of typically 1200 mm to 2000 mm within the vasculature depending on whether an ipsilateral, contralateral or radial approach is chosen. In this respect, a wire 4 tapering distally to a fine wire at its tip can navigate to the pedal arteries and around the pedal arch between the dorsal and plantar arteries. However, the invention is not limited to pedal or other peripheral applications and could, for example, be used in coronary applications, where the ability of the wire 4 to navigate to and to excavate within tortuous small-diameter arteries is also beneficial.

The diameter of the distal section of the wire 4 will determine the flexibility of the wire 4 and its ability easily to conform to the shape of the anatomy through which it is intended to pass. Thus, for example, in a tortuous (pedal or coronary) anatomy, a distal section of a diameter of 0.005" to 0.007" combines flexibility with the ability to excavate occlusive material.

The activation unit 2 includes user controls 6 and optionally also a display. The activation unit 2 further comprises a distal hand toggle 8 that a user can turn about the central longitudinal axis of the unit 2 and of the wire 4. In particular, the activation unit 2 can slide over the wire 4 and can be coupled to the wire 4 at a plurality of longitudinally spaced locations by applying torque to turn the toggle 8. To effect coupling, the toggle 8 acts on a coupling such as a collet within the activation unit 2 that surrounds and is coaxial with the wire 4. When the toggle 8 is tightened, the collet grips the wire 4 to transmit ultrasonic energy from an integrated ultrasonic transducer within the activation unit 2, optionally via an amplifier horn that is coupled to the transducer. The wire 4 could be coupled directly to the transducer in some embodiments, in which case the horn may be omitted.

The toggle 8 is reversible to release the activation unit 2 from the wire 4. Provision is thereby made to interchange wires 4 of different dimensions, configurations, or materials for different purposes. There is also the possibility of interchanging the transducer or the horn within the activation unit 2.

FIG. 1 shows a disaggregated arrangement in which an ultrasonic signal generator 10 is separate from the activation unit 2. In this example, the ultrasonic signal generator 10 is connected to the activation unit 2 by a connector cable 12. In alternative arrangements the ultrasonic signal generator 10 may be incorporated into the housing of the activation unit 2. The example shown in FIG. 1 has an externally powered ultrasonic signal generator 10 and therefore comprises a power cable 14 that connects to an external source of electrical power. Alternative embodiments may be powered by internal batteries, which can, e.g., be incorporated into the ultrasonic signal generator unit 10 or into the activation unit 2.

In general, the components of the system are preferably portable and are more preferably hand-held. The components may be wireless, rechargeable, reusable, and recyclable. Any external cable 12, 14 for conveying power or signals may be coupled through a slip ring to allow free rotation of the cable 12, 14 and to avoid entanglement with the wire 4 or it may provide a conduit for the proximal portion of the wire 4.

A semi-automated control system can control or modulate the signal from the generator 10 applied to the transducer and horn of the activation unit 2 and hence to the crossing wire 4 based on feedback from the wire-tissue interaction in order to control the signal being transmitted to adjust for losses due to damping or increased resistance or modulating applied force. Visual and haptic feedback indicators can offer visual, audio and/or tactile feedback to the user regarding the status of the device, the nature of the tissue being ablated and indicate the level of force that can be applied to effect ablation and disruption of the tissue and progression of the crossing wire.

The system may contain a means to provide a manual override to assist control of the amplitude of vibration delivered to the distal tip. This allows the system to be controlled by the user operating the device in the course of the procedure, through controllers and user input mechanisms located on the generator and transmission unit or to be controlled autonomously.

As will be explained, the distal end of the wire 4 is suitably also optimised for tracking through anatomies under ultrasound imaging modes, as well as having marker bands to highlight position under x-ray. It may have radio-opaque markers to indicate the working length and the crossing tip of the wire.

Figure 2:
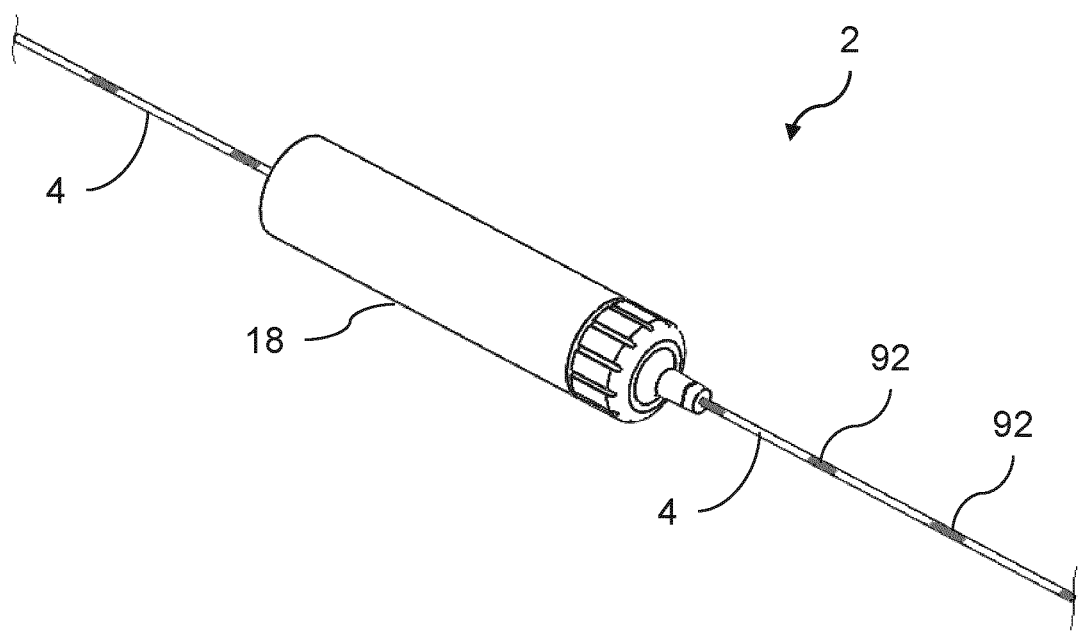
FIG. 2 is a perspective view of a hand-held ultrasonic activation unit and a wire with locating markings.

FIG. 2 shows how the wire 4 may be etched or otherwise marked with a series of optimum zonal markings 92 to guide the user in choosing lengths of the wire 4 that encourage distal activation. The user can then align the coupling of the activation unit 2 with the zonal markings 92 on the wire 4, optionally using other markings appropriately located on the housing 18 of the activation unit 2. This approach applies to both straight-through embodiments in which a proximal portion of the wire 4 emerges from the housing 18 of the activation unit 2 axially and other embodiments in which a proximal portion of the wire 4 emerges laterally at a position along the length of the housing 18.

The markings 92 address a challenge in the control of the system, namely the manner in which ultrasonic energy is coupled to the wire and the importance at locating the point of connection at specific regions that will couple best. The markings 92 placed on the proximal segment of the wire 4 ensure that this alignment is clear to the physician. These markings 92 also facilitate the physician reconnecting the activation unit 2 to the wire 4 at different locations during a procedure.

To address visibility and alignment for excitation, the markings 92 may be aligned with a reference point on the activation unit 2, for example a reference point on a strain relief feature at the distal end of the housing 18 to denote the best point of location. Visualisation of the markings 92 may be improved by adding illumination and/or a transparent or translucent window to the activation unit 2, for example positioned on a distal strain relief feature of the unit 2.

The markings 92 are apt to be applied by laser etch beading or other means, such as the application of a coating and/or a jacket, to mark the surface of the wire 4 in a way that allows the user to discriminate the best points of connection along the length of the wire 4. It is considered that modifying the oxide surface layer or the finish of the wire 4 is the best way to achieve this. The period or longitudinal spacing of these markings will be λ/2 and their length will be a function of the efficiency of coupling energy into the wire 4, which is also a function of its mechanical and dimensional properties.

In an example of the invention, the markings 92 on the wire 4 could indicate any of a plurality of lengths where the distal section of the wire 4 emerging from the housing 18 of the activation unit is at or near a resonant length and the proximal section is not at a resonant length. In other words, attachment zone markers 92 are positioned optimally on the wire 4 such that, when coupled to the acoustic source, the length of the distal portion from the coupling point to the distal tip is equal to a resonant length whereas the length of the proximal portion from the coupling point to the proximal tip is equal to a non-resonant length. In practice, these markings 92 may be located at positions tailored to the system to take into account bends and other design features that may affect the resonant response.

When using ultrasonic energy to excite the wire 4, it is desirable to optimise displacement amplitude in the distal tip portion of the wire to excavate a lesion. Conversely, it is desirable to minimise displacement or movement of the proximal end of the wire, which is outside the patient's body and indeed may hang freely from the proximal side of the activation unit 2.

To achieve this, the distal length of the wire 4 from the distal tip to where the activation unit 2 is coupled to the wire 4 should be an odd multiple of a quarter wavelength of the ultrasonic wave. This creates a standing wave in the wire with a vibrating antinode at the distal tip, hence maximising the amplitude of vibration at the distal tip.

Consequently, locating the distal end of the transducer at odd multiples of the quarter wavelength from the distal tip of the wire 4 will maximise vibration at the distal tip. Conversely, ensuring that the length of the proximal section is a multiple of half the wavelength from the transducer fixation will minimise vibration at the proximal end of the wire 4.

When coupled to the ultrasonic transducer 20 in the activation unit 2, a wire 4 of the invention undergoes axial ultrasonic vibration and can be considered as a fixed-free rod under longitudinal or axial vibration. The natural frequencies of a fixed-free rod under longitudinal or axial vibration are given by the expression:

$$\omega_n = \left(\frac{2n-1}{2}\right)\frac{\pi c}{L}, n = 1, 2, 3, \ldots$$

where c=the speed of sound in the wire material;
L is the length of the rod; and
ω=natural frequency of the system=2πf The ultrasonic activation unit 2 applies a constant known frequency and the speed of sound c of the wire 4 can be experimentally measured or approximated by the expression:

$$c = \sqrt{\frac{E}{\rho}}$$

where E=Youngs Modulus of the wire material; and
ρ=density of the wire material

For a system that applies a constant or near-constant frequency, the wire 4 lengths, L, at which resonance will occur are given by:

$$L = \frac{2n-1}{4}\lambda, n = 1, 2, 3, \ldots$$

Indeed, in a through-wire system, from the point of connection of the wire 4 to the transducer, the wire 4 can be considered as two fixed-free rods undergoing longitudinal axial vibration. One rod extends distally and the other rod extends proximally from the activation unit 2.

As an example, a particular nitinol alloy has a speed of sound of approximately 3400 m/s. For a drive frequency of 40 kHz, the wavelength A can be calculated to be approximately 85 mm. Resonant lengths can therefore be determined and marked at optimum positions on the wire 4. The wavelength further impacts on the selection of taper locations and taper lengths along the wire 4.

FIGS. 3 to 7 show various preferred and optional features of the wire 4.

In general, the wire 4 has features to allow it to integrate with the handheld activation unit 2. For example, location markers are provided to guide optimal positioning and attachment of the activation unit 2 to facilitate attachment and release at a plurality of longitudinal locations. Thus, over a significant length of its proximal section, a series of optimum attachment locations are etched or otherwise marked on the wire 4 to guide the user in locating and selecting the optimum attachment locations for distal ultrasonic transmission from the activation unit 2. The housing 18 of the activation unit 2 can also have a marker that can be aligned with the wire 4 marking prior to coupling.

As with all endovascular wires, a balance between flexibility or 'trackability' and rigidity or 'pushability' is required. However, unlike passive wires, the wire must be able to transmit ultrasonic energy to the distal region in order to assist in crossing lesions. In this way, the wire 4 functions as an excavator, not just at its tip but also along part of its length. The wire 4 has a distal land length that acts radially as a lateral excavation device for opening an aperture. The wire may have distal shaped lengths to amplify radial excavation.

The wire 4 includes regions where the geometry tapers to affect a change in diameter, either from a larger to a smaller diameter or from a smaller diameter to a larger diameter. In regions where tapers are required and at other locations, sections may be welded or otherwise joined together end to end. Such welds or joins must be able to withstand the stresses arising from transmission of ultrasonic energy in addition to normal modes of bending and cyclic fatigue. Alternatively, the entire wire 4 or parts of the wire 4 could be ground or similarly processed to achieve the desired geometry.

The wire 4 may therefore be fabricated from sections welded together end-to-end. For example, a proximal section may be machined as a standard diameter to provide for amplification as well as to provide a standard connection for a proximally-loaded activation unit 2. The proximal section can be welded to one of a selection of different diameter wires that may have custom distal ends and tips. Thus, sections may be chosen and combined in various ways. This beneficially reduces the requirement to hold stock of various wire diameters as sections of a few different wire diameters may be assembled to produce wires 4 of many required configurations. Welding the proximal segment to the distal segment facilitates more efficient manufacturing and more efficient transmission if post-processing is performed on the wire, and allows welding of different materials to a proximal NiTi base if desired.

Ideally, tapers can be chosen to begin at lengths equal or nearly equal to multiples of the half wavelength of the wire system. This places the start of the tapers at anti-nodes of a standing wave in the wire 4, where the amplitude of vibration is at a maximum. Preferably, the lengths of the tapered sections are chosen to be equal or nearly equal to half wavelengths of the resonant system. In general, welds or joins should be located at longitudinal positions where the stress is at a minimum. As the welds or joins are at locations of low stress, the loads applied to them in the course of activation of the wire will not lead to catastrophic fatigue failure.

Figure 3:
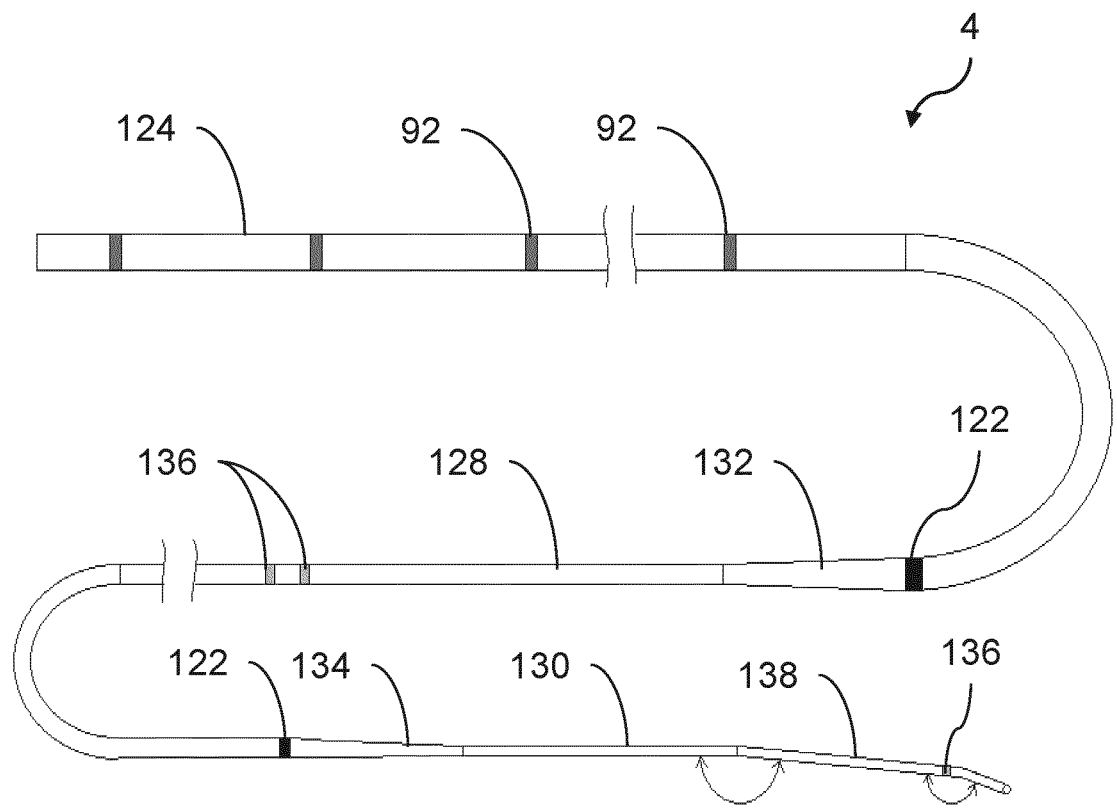
FIG. 3 is a schematic side view of a wire in accordance with the invention.

The wire 4 shown in FIG. 3 comprises a proximal section 124, a central or intermediate section 128 and a distal excavating section 130 for crossing a lesion. The intermediate section 128 is narrower than the proximal section 124 but is wider than the distal section 130. The intermediate section 128 is therefore joined to the proximal section 124 by a tapering proximal transition 132 and to the distal section by a tapering distal transition 134. Each section is welded to the next by a weld 122 on the proximal side of the respective transitions.

The proximal section 124 has a series of longitudinally spaced zonal markings 92 like those in FIG. 2 to guide the user in choosing wire lengths that encourage distal activation and that discourage proximal activation. The wire 4 further comprises radio opaque marker bands 136 to aid tracking of the intermediate 128 and distal sections 130 within a patient's anatomy during the procedure. These various markers 136 are apt to be created by plasma vapour deposition, atomic layer deposition or sputtering, for example of sputtered gold, to resist ultrasonic loading.

The proximal section 124, the intermediate section 128 and the distal section 130 are all generally straight and in mutual alignment along a central longitudinal axis of the wire, albeit substantially flexible to be bent along their length. However, a compound distal end portion 138 of the wire 4 has a shape set to be bent away from the general axis of the wire 4 in the remainder of the distal section 130. These bends or heat set shapes enhance lateral motion in addition to longitudinal motion of the wire 4.

Figure 4:
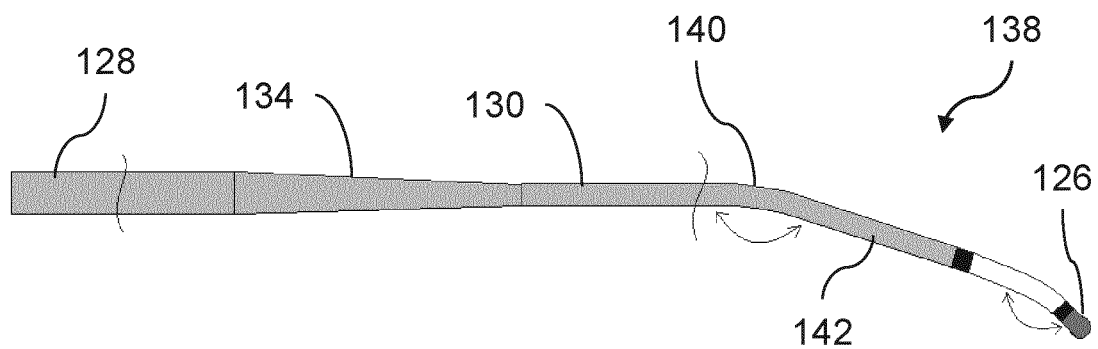
FIG. 4 is an enlarged side view of a distal end portion of a wire in accordance with the invention.

Specifically, as also shown in FIG. 4, the distal end portion 138 comprises an inboard angled leg 140 and an outboard distal tip 126 at the distal end of the angled leg 140. The leg 140 is inclined relative to the general axis of the wire 4 and the distal tip 126 is inclined relative to the angled leg 140. The distal tip 126 may be a bulbous or otherwise enlarged feature as 25 shown in FIG. 4 and a coating 142 may extend part-way along the length of the angled leg 140, leaving the distal extremity of the angle leg 140 and the distal tip 126 uncoated.

In this example, the distal tip 126 is inclined further than the angled leg 140 away from the general axis of the wire 4. Thus, the distal tip 126 and the angled leg 140 are both inclined in broadly the same direction away from the general axis of the wire 4. In other examples, however, the inclination of the distal tip 126 is closer than the angled leg 140 to the general axis of the wire 4. Potentially, the distal tip 126 could even be approximately parallel to the general axis of the wire 4 in the remainder of the distal section 130.

To recap, the total length of the distal portion of the wire 4 from the distal tip 126 to the connection point or coupling of the activation unit 2 may be equal to the resonant length for the wire 4. Ideally the taper length is equal to a multiple of half the wavelength. The diameters of the various sections of the wire 4 are chosen for an optimal balance between pushability and trackability, in addition to being able to allow follow-on devices of standard dimensions to use the wire 4 as a guidewire.

In this example, the wire 4 includes angled parts positioned at locations to enhance steerability of the wire 4 when tracking to the location of a lesion. By way of example, the angled leg 140 may be 15 mm to 25 mm in length and the distal tip 126 may be 2 mm to 5 mm in length. The angled leg 140 facilitates steering through the anatomy whereas the distal tip 126 facilitates tracking through small-diameter lesions. The angle between the angled leg and the remainder of the distal section 130 is typically 10° to 40°. This angle provides a means to navigate into branches but is not so great as to promote stresses that exceed the fatigue limit of the wire 4. The angle between the distal tip 126 and the angled leg 140 is typically 10° to 30°. This enables navigation in diseased small-diameter vessels.

The wire 4 may be heat-treated, for example by annealing after machining and shaping the tip 126, to optimise its microstructure to resist fatigue.

Visibility of the wire 4 under x-ray or other imaging mode may be enhanced with the addition of radiopaque marker bands or coatings 136 chosen to optimize visibility under well-established imaging modes. The wire 4 may also have coatings 142, such as hydrophilic coatings, to reduce friction with surrounding catheters or tissue.

Figure 5:
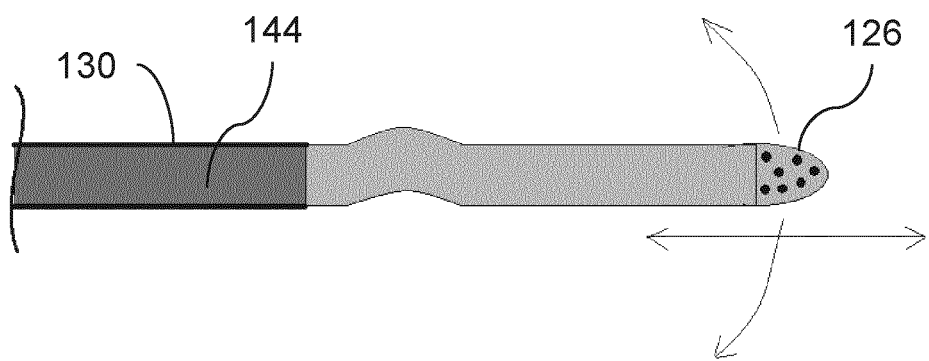
FIG. 5 is an enlarged view of a distal end portion of a wire in a variant of the invention.

FIG. 5 shows that the wire 4 may have a distal coil or polymer jacket 144 attached or bonded over the distal section 130. The jacket shown here terminates distally just before a bend in the wire 4 that facilitates deflection of the distal tip 126. The distal tip 126 of the wire 4 may be coated or processed to harden the surface or increase its ablative properties.

Figure 6:
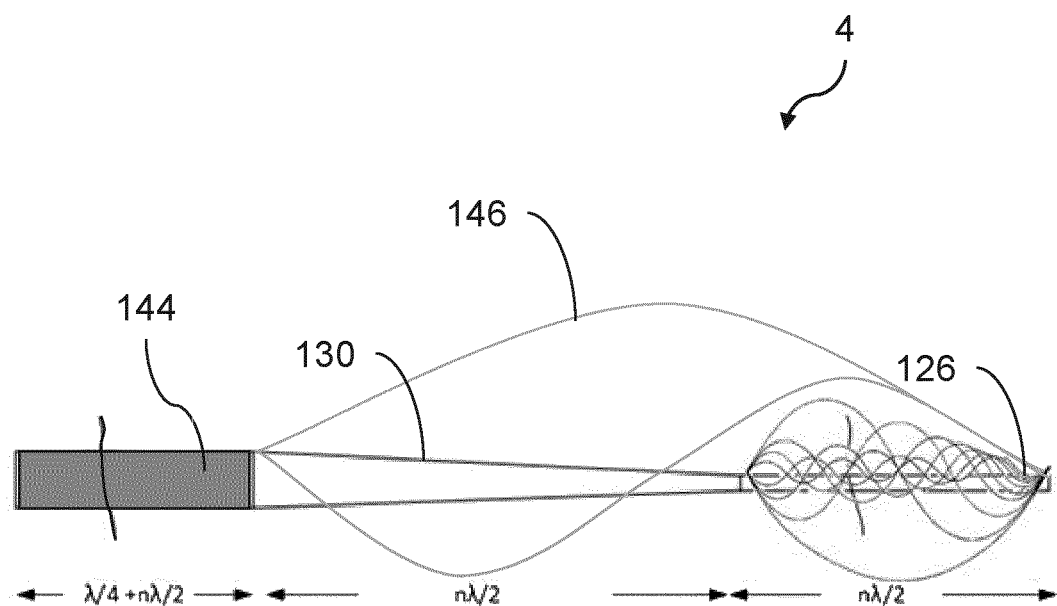
FIGS. 6 and 6a are side views of a wire of the invention, showing its response to excitation.
Figure 6A:
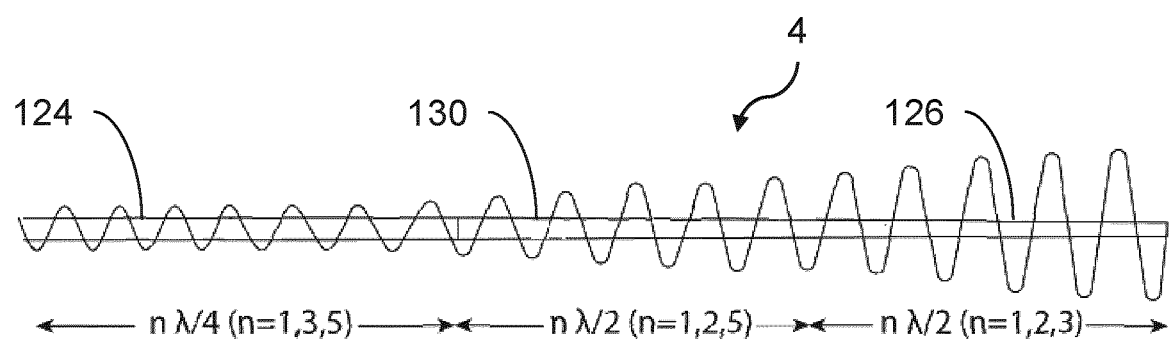

FIGS. 6 and 6a show a wire 4 that has a substantially straight proximal section or land 124, a distally-tapering intermediate section 130 and a substantially straight excavating part or land providing a distal tip portion 126 for crossing a lesion. By virtue of the taper of the intermediate section 130 between them, the distal tip portion 126 has a smaller diameter than the proximal section 124. For example, the proximal section 124 may have a diameter of 0.43 mm and the distal tip portion 126 may have a diameter of 0.18 mm or 0.25 mm. The taper in the intermediate section 130 is slight and so is greatly exaggerated in these drawings. The tapering intermediate section 130 may extend over a multiple of $\lambda$ in length or a fraction of $\lambda$ in length, that fraction preferably having with a numerator of 1 and an even denominator—for example in the sequence ½, ¼, ⅛ . . . —whereas the distal tip portion 126 may have a length of $\lambda/2$ or a multiple of $\lambda/2$ or a fraction of $\lambda/2$ such as $\lambda/4$.

The overall geometry of the wire 4 including its nominal diameter and length and the driving frequency of the system are determined by the characteristic speed of sound in the material of the wire. This characteristic is a function of that material's properties and its geometry. The dimensions of the straight and tapered sections of the wire are machined at functional intervals of wavelength.

As an example of nitinol with a Young's Modulus of approximately 75 GPa, $\lambda$, $\lambda/2$ and $\lambda/4$ are determined to be 84 mm, 42 mm and 21 mm in this example. The chosen frequency will produce harmonics along the length of the wire and the loading of the tip of the wire will assist in establishing standing waves for non-characteristic lesions. The distal section 126 can be tapered or can be uniform in diameter along its length. The system may produce lateral and longitudinal displacements over a range of frequencies away from that of the drive frequency, often occurring at sub-harmonics of the frequency in the distal section 126.

As an example, which does not preclude other dimensional values, a wire with a core cross section diameter of 0.43 mm has a tapered section 130 optimally located to transition to a distal wire diameter to 0.18 mm. The lengths of each section of the wire can be chosen to have a longitudinal resonant mode at or near the driving frequency, such as 40 kHz, with strong sub-harmonics at or near 20 kHz, 10 kHz or others. Through appropriate design, there are neighbouring lateral modes near 40 khz and 20 khz or others. There may be amplification across the taper by a factor of approximately 2.4 or other suitable value. As the wire emerges from a catheter or sheath, additional lower-frequency lateral vibrations may be induced through a cantilever action.

As a result, through appropriate selection of wire material, geometry and distal design features, desirable lateral modes will be energised even when the wire is driven with longitudinal vibrations. In unison, both the longitudinal and lateral vibrations contribute to excavation of the lesion and result in the wire opening an aperture or lumen in the lesion whose internal diameter is substantially greater than the wire diameter.

In terms of length, the overall length of the wire may be a function of an odd multiple of λ/4. The active length, being the distance from the proximal connection point to the distal tip of the wire, may also be a function of an odd multiple of λ/4.

The purpose of the tapered transition 130 is to provide gain and to sustain the transmission of energy through the wire. The tapered section will also affect how a lateral mode of displacement may be established in the distal land section 126 of the wire.

The point at which the taper is introduced may also assist with facilitating a change of materials between one part of the wire and another, which could create a differential in wavelength between the distal and proximal segments.

Tapered transitions may vary in diameter in a stepped, exponential, radial or linear manner. For the purpose of amplification, the change in the cross-sectional area represents a level of gain in both lateral and longitudinal displacement amplitudes in the wire. The length and the diameter of the distal section 126 will determine the mode and magnitude of displacement in axial and radial directions.

As the goal of the activated wire 4 is to cross and excavate a lesion, its dimensions are optimised with the purpose of excavating as large an aperture as possible at a given input. In this respect, FIG. 6 shows that the distal section 126 of the wire 4, once activated, moves in a primary longitudinal mode, moving in and out, and also in a radial direction which maps out and excavates a greater volume at the distal end through the longitudinal movement of the wire 4. The distal section 126 of the wire 4 is also seen to move through lateral and undulating movements at or near the drive frequency and secondary modes of differential harmonics, dependent on the activating frequency and also the length of the distal section 126. These wave forms may interfere with each other and be more or less effective in excavating material at different moments.

FIG. 6 further shows how the distal end section 126 of the wire 4 may excavate an aperture whose diameter is greater than the diameter of the wire and so create a larger lumen through which therapies may be introduced to a lesion. In this example, again, a catheter sleeve or a polymer jacket 144 terminates before an unjacketed distal section 130 of the wire. The distal section 126 of the wire 4, once activated, moves in a primary longitudinal mode, moving in and out, and also in a radial direction which maps out and excavates a greater volume at the distal end through the longitudinal movement of the wire 4. The distal section 126 of the wire 4 is also seen to move in other modes through lateral and undulating movements under the resonant wave 146 and secondary modes of differential harmonics, dependent on the activating frequency, the length of the distal section and the tortuosity of the anatomy.

Thus, when activated with ultrasonic energy, the wire 4 acts as an excavation tool for excavating material distal to the distal tip of the wire 4 by virtue of longitudinal movement and then through the offset translation or lateral motion of the wire 4 within the vasculature which provides a lateral offset. Thus, the wire 4 abrades the inner surface of the occlusion not just at its distal tip but also along some of its length extending proximally from the distal tip and so forms a wider aperture for the passage of follow-up therapeutic devices over the wire 4. As the wire 4 extends beyond the distal end of the lesion, the lateral displacement continues to excavate within the body of the lesion and so forms a larger lumen.

Figure 7:
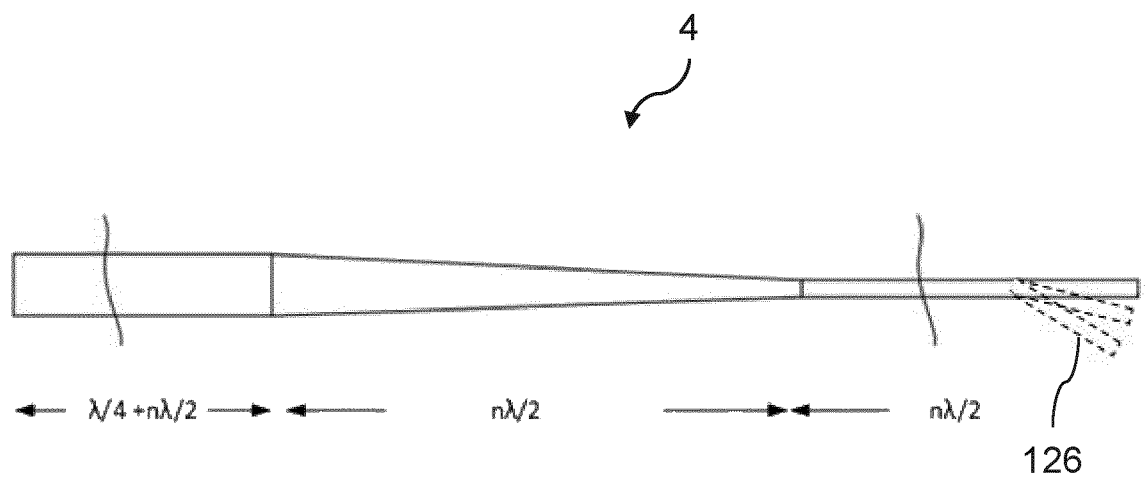
FIG. 7 is a schematic side view of an active wire having an angularly-offset distal end portion.

FIG. 7 shows a wire 4 that is formed or shaped to have an angularly-offset distal excavating section for crossing a lesion. In this embodiment, the distal section is not straight but is angled by virtue of a heat-set shaped tip 126. The dimensions of the tip 126 are optimised to provide improved performance in terms of steering to a lesion and excavation of the lesion. In particular, the angle of the tip 126 relative to the longitudinal axis of the distal section and the length of the tip 126 determine the ability of the wire 4 to turn into a specific side-branch vessel. The angle and the length of the tip 126 also affect the manner in which the wire 4, once activated, will excavate a section of stenosed material If the dimensions of the tip 126 are characteristic of a harmonic, e.g. λ/8 or about 11 mm in length, the wire 4 will open out a significantly larger tunnel in a lesion than say a 25 mm tip section. The amplitude of the waveform and the number of times the distal section of the wire 4 is passed through a calcific section will determine the diameter of the tunnel that is excavated.

The wire 4 may not necessarily be shaped or angled at its tip but where it is shaped or angled at its tip, the angle is chosen carefully. If the angle of the tip 126 is too great, it will create a larger lever arm and so could fatigue the wire 4 excessively; conversely if the angle of the tip 126 is too small, then the wire 4 may not be steerable effectively. In this respect, FIG. 7 shows that the tip 126 may be offset from the longitudinal axis of the wire 4 by about 15° to 45°, allowing the tip 126 to disrupt and excavate a greater volume of a lesion. The tip 126 is suitably heat-treated, for example at over 500° C. for less than 10 minutes, in order to create a microstructure that is reliably resistant to crack propagation and hence to fatigue.

Figure 8A:
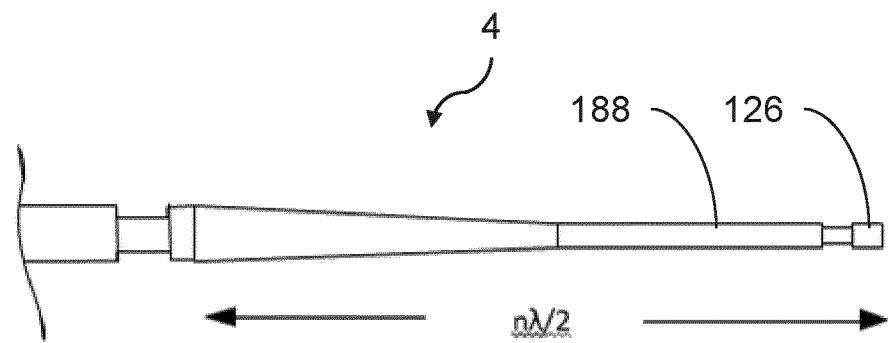
FIGS. 8a and 8b are schematic side views of a further active wire of the invention, including marker bands.
Figure 8B:
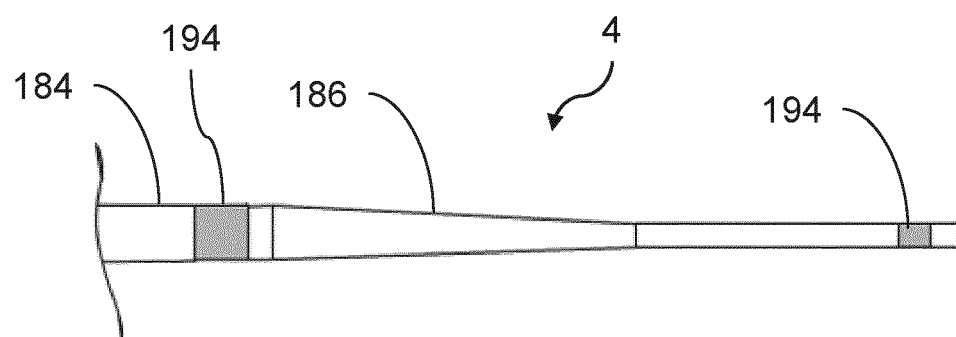

FIGS. 8a and 8b show how visibility of the location of the wire 4 in the patient's body may be enhanced by the use of marker bands 194, for example of gold. Such marker bands 194 may, for example, be fixed at locations close to (for example, about 3 mm from) the distal tip 126 of the wire 4 and also from the distal end of the proximal section 184, just before the start of the tapered intermediate section 186. The marker bands 194 are placed at locations of minimal load in use of the wire 4. This minimises the possibility that the marker bands 194 could become detached or that the wire 4 could fail at those locations. The marker bands 194 are apt to be flush-fitted into circumferential grooves that are ground around the wire 4.

Figure 9:
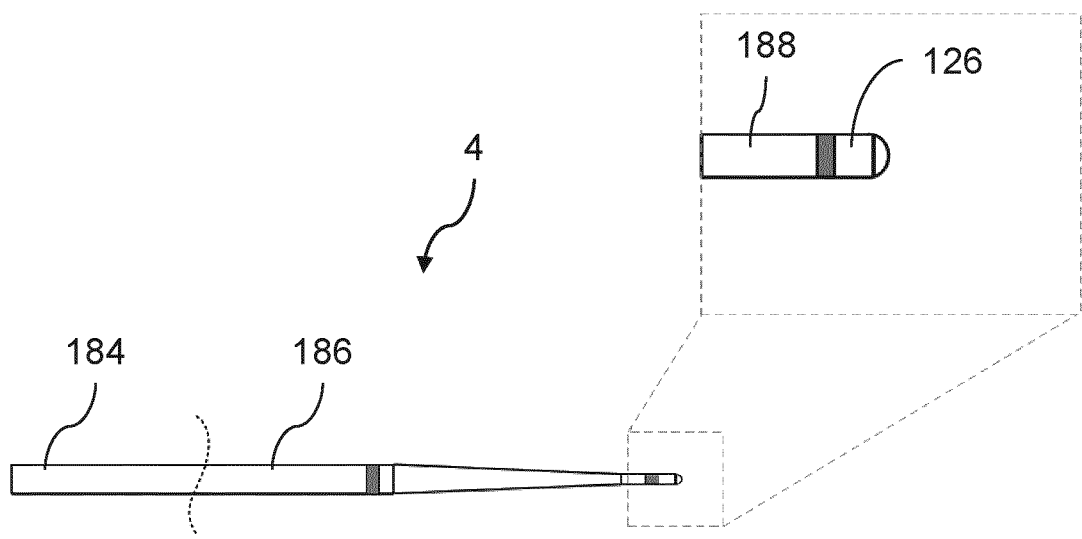
FIG. 9 is a schematic side view of another active wire of the invention.

FIG. 9 shows a variant in which the distal tip 126 of the wire 4 is rounded, with no sharp transitions. By way of example, in this instance the proximal section 184 may be 1800 mm long, the tapered intermediate section 186 may be 84 mm long and the distal section 188 may be 10 mm long. Again, marker bands 194 encircle the wire 4 close to the distal tip 126 of the wire 4 and the distal end of the proximal section 184.

Figure 10:
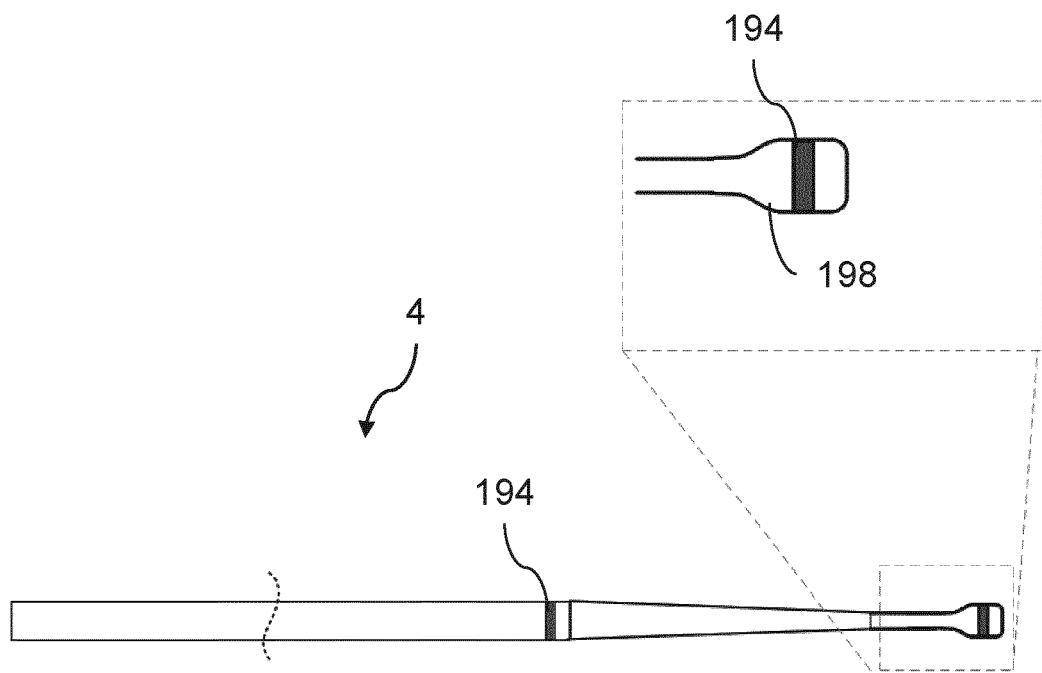
FIGS. 10 and 11 are schematic side views of other active wires of the invention, each having an enlarged, bulbous distal tip
Figure 11:
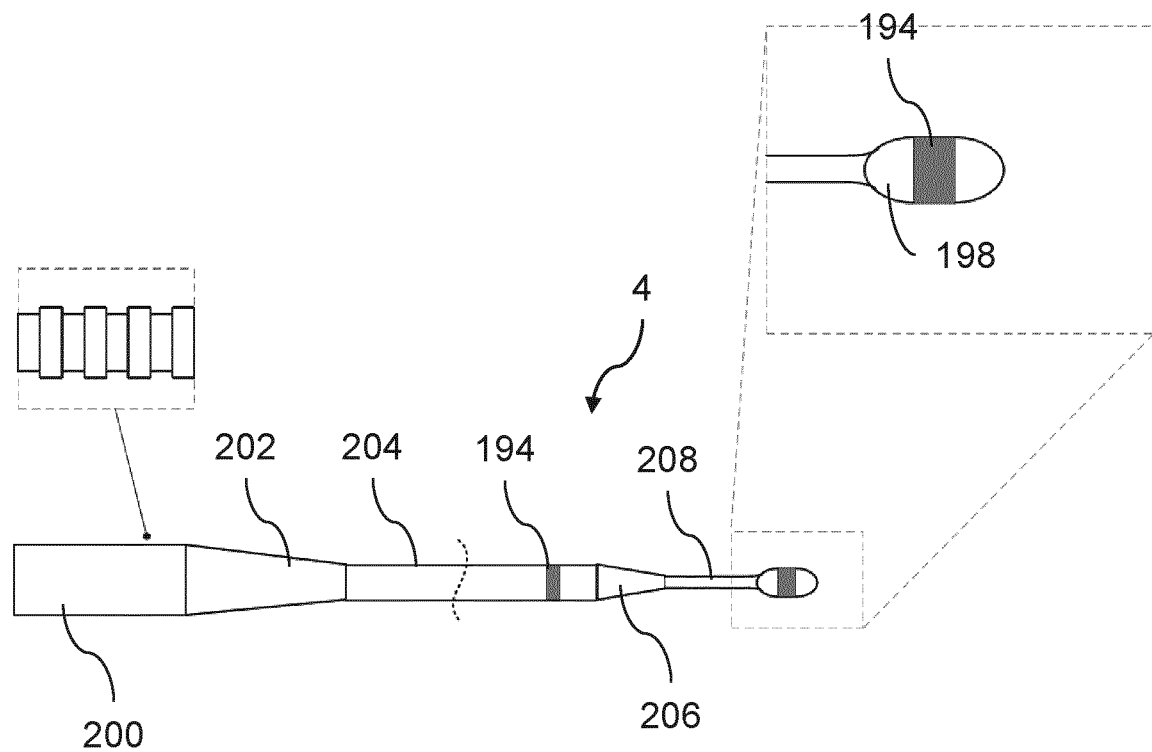

FIGS. 10 and 11 show other variants of the wire 4 that each have a bulbous distal tip 198, which is rounded to avoid sharp transitions but could instead be chamfered or faceted, preferably with obtuse angles between facets, with distally-converging facets that ease passage of the wire through the anatomy. Enlargements such as bulbs may be located at the distal tip and/or be spaced slightly from the distal tip, and could cover a radiopaque coil or other materials.

The bulbous tip 198 may, for example, be 3 mm to 4 mm in length and may have a diameter of just over 0.4 mm, or from 0.010" to 0.035" for example. Apart from its bulbous tip 198, the wire shown in FIG. 10 is otherwise analogous to the wire 4 shown in FIG. 9. Again, the wires 4 shown in FIGS. 10 and 11 have circumferential marker bands 194 that may be flush-fitted into circumferential grooves ground around the wire 4. Conveniently, as shown, the bulbous tip 198 may be encircled by one of the marker bands 194.

In the example shown in FIG. 11, the wire has a proximal portion that comprises a straight section 200 and a distally tapering section 202. The straight section 200 may have a ridged or otherwise textured surface as shown, to improve engagement with an activation device. The proximal portion is welded to an intermediate portion that constitutes most of the length of the wire 4. The intermediate portion also comprises a straight section 204 and a short distally tapering section 206. A marker band 194 is shown encircling the straight section 204 close to the distally tapering section 206 of the intermediate portion 194. Finally, a short, narrow distal section 208 extends distally from the intermediate portion 186 to the bulbous tip 198.

Figure 12:
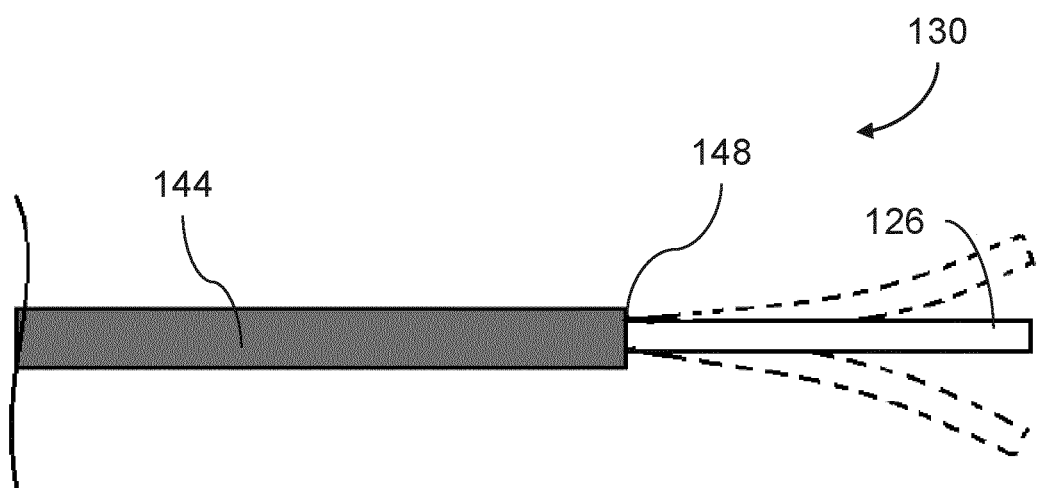
FIG. 12 is a side view of a wire of the invention, showing an effect of jacketing the wire.

FIG. 12 illustrates how jacketing or thickly coating the wire, for example with a polymer jacket or coil 144, leaves a desired distal length clear or unjacketed and free to oscillate laterally as shown. The effect of jacketing or coating could also be emulated by a catheter around the wire 4. The distal extent of jacketing has been found to control the aperture created by the distal excavating section 130 of the wire 4. The wire 4 excavates a lesion up to the collar or edge 148 at the distal end of the jacket 144. It has been found that if the unjacketed distal length of the wire is not sufficiently long, an aperture of not much more than the diameter of the wire may be created in a lesion, inhibiting even the progression of the wire through a blockage.

In particular, jacketing the wire 4 below or beyond a resonant or harmonic length, so that the distal edge 148 of the jacket 144 does not coincide with a resonant or harmonic length, hinders formation of an aperture. Conversely, jacketing the wire 4 up to a resonant or harmonic length, so that the distal edge 148 of the jacket 144 substantially coincides with a resonant or harmonic length, allows the wire 4 to excavate a larger aperture.

Figure 13A:
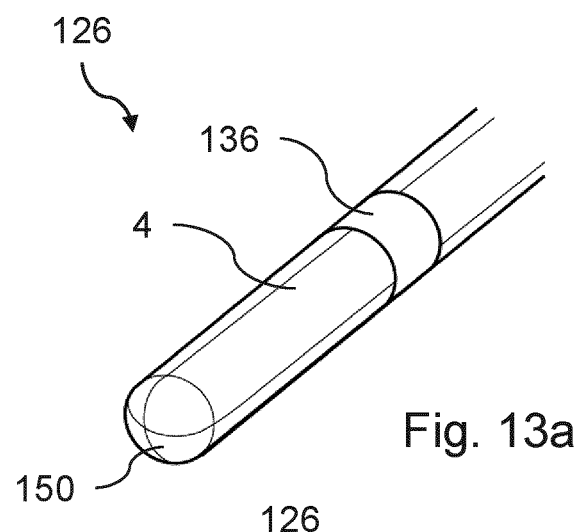
FIGS. 13a, 13b, and 13c are schematic perspective views, showing end portions of a wires in variants of the invention.
Figure 13B:
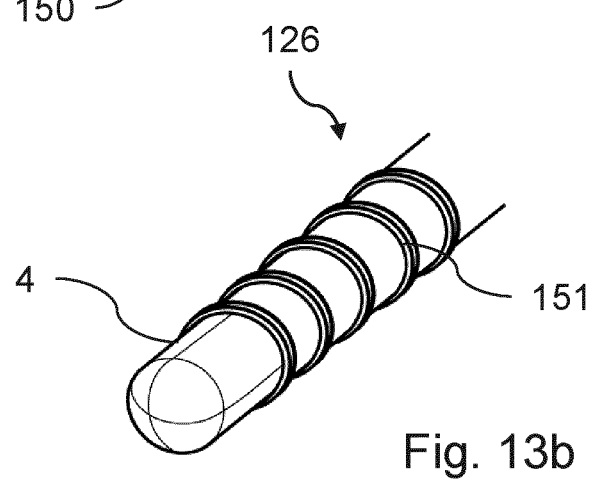
Figure 13C:
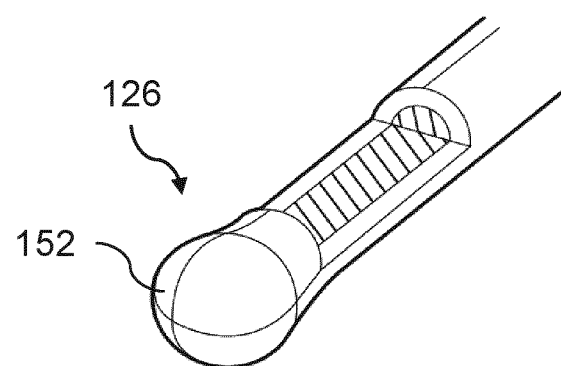

FIGS. 13a, 13b, and 13c show a selection of arrangements of the distal tip 126. FIG. 13a shows the wire 4 encircled by a radio-opaque band 136 and provided with a rounded bull tip 150, for example of beryllium. FIG. 13b shows a radio-opaque coil 151 welded around the distal tip section 126 of the wire 4. FIG. 13c shows an oversized beryllium tip 152 to increase effectiveness when crossing long calcific sections. The distal tip section 126 may be heat-treated to increase its fatigue resistance.

Figure 14A:
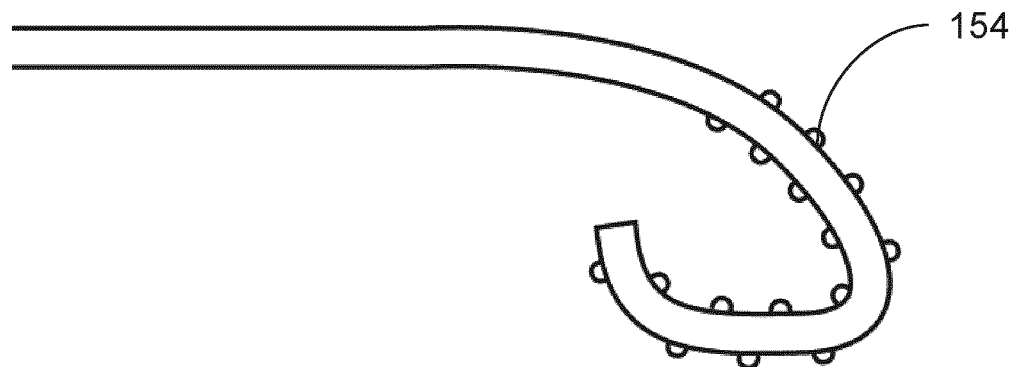
FIGS. 14a, 14b, and 14c are schematic perspective views, showing end portions of a wires in further variants of the invention.
Figure 14B:
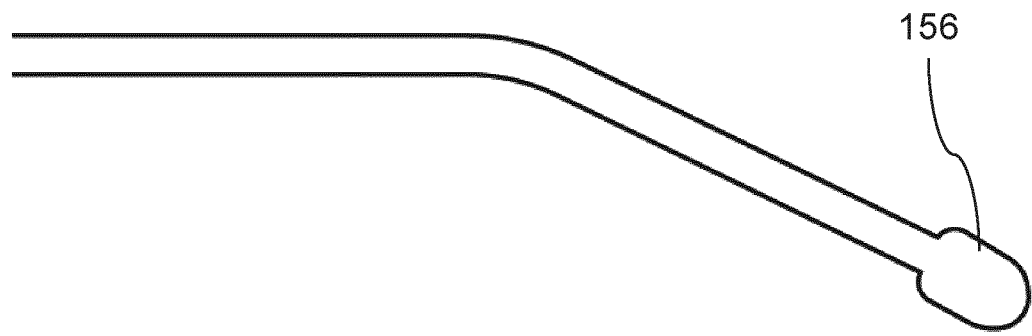
Figure 14C:
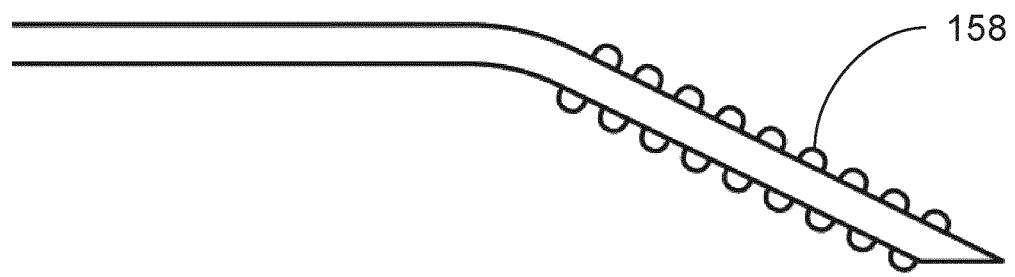

FIGS. 14a, 14b, 14c show other arrangements of the distal tip 126. FIG. 14a shows a looped tip 154 with an outer surface that is coated or otherwise modified to optimize drilling or excavation over the loop rather than being confined to a tip. The loop may also aid navigation to the site of a blockage. FIG. 14b shows a diamond-coated tipped burr 156. FIG. 14c shows a drilling end tip 158 or segment that is coated with a diamond and/or carbide coating. Coatings and hardened materials such as these provide for aggressive machining of lesions.

In general, wires 4 of the invention are apt to be made of superelastic alloys, such as nitinol (nickel-titanium), which are known to have preferential properties in the transmission of ultrasound while providing a balance of flexibility and pushability. Linear elastic nitinol arising from advances in processing alloys of nickel and titanium may also be used for wires of the invention, as can beta titanium. Surface finishes and coatings applied to the wires 4 may include resilient fluoropolymers and hydrophilic coatings to reduce friction.

Many other variations are possible within the inventive concept. For example, a coating may be provided along a discrete segment of the wire, such as by coating a mid-section of the length of the wire to leave distal and proximal end portions of the wire uncoated for excavation and for clamping an activation unit, respectively. Continuous and broken segments of coating along the length of the wire may allow for selective clamping and unclamping of an activation unit at desired positions.

PTFE or alternative polymeric jackets may be employed to reduce friction and risk of damage to the interior of a guide catheter Polymer jackets may be employed in a distal section for improved radiopacity, more generally along the wire to provide for lubricity, or to provide a marking point to connect to a transducer of an activation unit.

Surface modification may involve addition of striations or serrations into the surface of the distal end portion to bite further into calcific lesions so as to assist excavation and resist damage. Such formations may be directional so to take advantage of the direction of motion and to amplify the efficiency of cutting or abrasion of the occluding material. Nevertheless, individual formations may have a smooth rather than sharp contours so as not to damage the vessel wall. Similarly, materials may be applied to the wire to create an additional abrading surface to assist in excavating material. Such materials may usefully reduce the area of the wire that is in contact with the lesion to promote cutting and to prevent calcified material blocking vibration and movement of the wire.

Drawn filled tubing (DFT) may be employed, in which a NiTi core is surrounded by a second metal that has different properties, for example stainless steel. As the relative thickness of that secondary layer can be controlled, it could be used to create marker bands for coupling or shaping of the wire, or for promoting lateral damping.

A jacket of a shaped alloy could provide for navigation and/or opacity. The use of a more ductile compliant outer jacket could avoid cold working of nitinol and the need for post-process thermal treatment.

Potentially, there could be multiple cutting planes defined by multiple lands at a distal tip or end region of a wire. This could facilitate different and potentially more anatomically-suited distal end gain as well as a second proximal land of possibly greater diameter to better work on the lesion. This is one way of creating multiple lateral excavation zones, others being different section diameters, different tapers and different excavation land profiles.

It is noted that the many features of the various embodiments described above are not limited to those specific embodiments only. A skilled person will be able to combine features from one embodiment with features of other embodiments wherever this is technically possible and makes sense from a practical point of view.

The invention claimed is:

1. A method of crossing through a lesion in a blood vessel by ultrasonically exciting a wire serving as an elongate waveguide element, the method comprising:
   inserting a distal section of the wire into a patient's vasculature, wherein the distal section extends proximally from a distal tip of the wire;
   coupling an ultrasonic transducer to the wire at a location selected from a plurality of locations along the wire, at any of which locations the ultrasonic transducer may be coupled to the wire to encourage activation of the distal section of the wire;
   bringing the distal section of the wire to a location of the lesion;
   inputting ultrasonic energy into a proximal section of the wire from the ultrasonic transducer, the ultrasonic transducer operating at a driving frequency that excites longitudinal resonance in the wire and generates longitudinal vibrations in the distal section, and that corresponds to a wavelength λ;
   amplifying the ultrasonic energy between the proximal section and the distal section by conveying the ultrasonic energy along a distally-tapering intermediate section of the wire that extends between the proximal section and the distal section;
   and
   generating lateral vibrations in the distal section over a range of frequencies in addition to the longitudinal vibrations, the lateral vibrations including sub-harmonic vibrations at frequencies of 1/2, 1/4 . . . 1/N of the driving frequency, causing the distal section to move in a primary longitudinal mode and in a secondary radial mode to excavate a lumen through the lesion around the distal section, the lumen having a diameter greater than a diameter of the distal section.

2. The method of claim 1, wherein the distal section has a length of substantially λ/2 or a multiple of λ/2.

3. The method of claim 1, wherein the distal section has a length of substantially λ.

4. The method of claim 1, wherein the intermediate section has a length of substantially λ/2 or a multiple of λ/2.

5. The method of claim 1, wherein the intermediate section has a length of an even-denominator fraction of λ/2 in the sequence λ/4, λ/8.

6. The method of claim 1, wherein the distal tip is bulbous or otherwise enlarged relative to the distal section.

7. The method of claim 6, wherein the distal section is unencapsulated by a catheter, sleeve or jacket.

8. The method of claim 1, further comprising delivering therapeutic devices over the wire to treat the lesion.

9. A method of crossing through a lesion in a blood vessel by ultrasonically exciting a distal tip section of a waveguide element, the method comprising:
   inserting the waveguide element into a patient's vasculature;
   bringing the distal tip section to a location of the lesion;
   coupling the waveguide element to an ultrasonic activation unit at one of a selected longitudinal location of a plurality of longitudinal locations along the waveguide element;
   uncoupling the waveguide element from and recoupling the waveguide element to the ultrasonic activation unit at another of the plurality of longitudinal locations along the waveguide element; and, at each of the longitudinal locations,
   inputting ultrasonic energy into a proximal section of the waveguide element at a driving frequency that excites longitudinal resonance in the wavelength element; and
   generating lateral sub-harmonic vibrations in the distal tip section in addition to longitudinal vibrations.

10. The method of claim 9, wherein the coupling of the waveguide element at a selected longitudinal location includes a location corresponding to one of a plurality of markings on the waveguide element that encourages distal activation.

11. The method of claim 9, further including interchanging the waveguide element with a waveguide element of different dimensions.

12. The method of claim 9, further comprising crossing through the lesion with the waveguide element.

13. The method of claim 12, further comprising retaining the waveguide element in the vasculature to serve as a guide wire for delivery of subsequent therapeutic devices to treat the lesion.

14. The method of claim 9, further comprising amplifying the ultrasonic energy between the proximal section and the distal tip section.

15. The method of claim 9, further comprising attenuating lateral vibration of the element proximally with respect to the distal tip section.

16. The method of claim 9, wherein the lesion is an occlusion in the blood vessel.

17. A method of crossing through a lesion in a blood vessel by ultrasonically exciting a distal tip section of a wire, the method comprising:
   inserting the wire into a patient's vasculature;
   bringing the distal tip section to a location of the lesion;
   coupling a source of ultrasonic energy to a proximal section of the wire at a selected longitudinal location along the wire, that location corresponding to one of a plurality of markings on the wire that encourages activation of the distal tip section;
   inputting ultrasonic energy into the proximal section of the wire at a driving frequency that excites longitudinal resonance in the wire;
   generating lateral sub-harmonic vibrations in the distal tip section in addition to longitudinal vibrations;
   crossing through the lesion with the wire; and
   delivering therapeutic devices to treat the lesion over the wire.

18. The method of claim 17, further including interchanging the wire with a wire of different dimensions.

* * * * *

UNITED STATES PATENT AND TRADEMARK OFFICE
CERTIFICATE OF CORRECTION

PATENT NO. : 12,059,162 B2
APPLICATION NO. : 17/662304
DATED : August 13, 2024
INVENTOR(S) : Finbar Dolan et al.

Page 1 of 1

It is certified that error appears in the above-identified patent and that said Letters Patent is hereby corrected as shown below:

In the Claims

In Claim 1, Column 19, Line 37, delete "A" and insert --$\lambda$--

In Claim 5, Column 19, Line 61, delete "$\lambda/8$." and insert --$\lambda/8$ . . . .--

In Claim 9, Column 20, Line 19, delete "wavelength" and insert --waveguide--

Signed and Sealed this
Twenty-sixth Day of November, 2024

Katherine Kelly Vidal
*Director of the United States Patent and Trademark Office*